(12) United States Patent
Moorleghem et al.

(10) Patent No.: US 6,375,458 B1
(45) Date of Patent: Apr. 23, 2002

(54) MEDICAL INSTRUMENTS AND DEVICES AND PARTS THEREOF USING SHAPE MEMORY ALLOYS

(75) Inventors: Wilfried Van Moorleghem, Lubeek; Anja Serneels, Diest, both of (BE); L. McDonald Schetky, Camden, ME (US)

(73) Assignee: Memry Corporation, Bethel, CT (US)

( * ) Notice: Subject to any disclaimer, the term of this patent is extended or adjusted under 35 U.S.C. 154(b) by 0 days.

(21) Appl. No.: 09/313,013

(22) Filed: May 17, 1999

(51) Int. Cl.[7] .............................. A61C 3/00; A61F 2/06
(52) U.S. Cl. .................... 433/2; 433/8; 433/20; 623/1.15; 623/1.16; 623/1.2
(58) Field of Search .............................. 433/8, 20, 22, 433/2; 606/198; 623/1.15, 1.16, 1.2

(56) References Cited

U.S. PATENT DOCUMENTS

| | | | | |
|---|---|---|---|---|
| 4,505,767 A | * | 3/1985 | Quin | 148/402 |
| 5,683,245 A | * | 11/1997 | Sachdeva et al. | 433/20 |
| 5,692,899 A | * | 12/1997 | Takahashi et al. | 433/20 |
| 5,843,244 A | * | 12/1998 | Pelton et al. | 148/563 |
| 5,863,360 A | * | 1/1999 | Wood et al. | 148/561 |
| 6,258,182 B1 | * | 7/2001 | Schetky et al. | 148/402 |

* cited by examiner

Primary Examiner—Nicholas D. Lucchesi
(74) Attorney, Agent, or Firm—Jerry Cohen; Harvey Kaye; Perkins, Smith & Cohen (57) ABSTRACT

Fabrication of metal medical instruments and devices from a shape memory alloy which provides greater flexibility in design and avoids the need for substantial cold working of the alloy which is required in other methods. The new process provides a ductile alloy for ease of forming and a unique heat treatment which renders the fabricated orthodontic and medical components highly elastic, with a high resistance to kinking and with good corrosion resistance. In addition, this new process produces orthodontic and medical components useful over the temperature range of from −20 to +40 degrees C.

24 Claims, 7 Drawing Sheets

MEDICAL INSTRUMENTS AND DEVICES AND PARTS THEREOF USING SHAPE MEMORY ALLOYS

FIELD OF THE INVENTION

This invention relates generally to the fabrication of orthodontic and medical instruments and devices and components thereof, and, more particularly to the fabrication thereof from a specially processed Nickel-Titanium shape memory alloy.

BACKGROUND OF THE INVENTION

The concept of using shape memory alloys for eyeglass components has been suggested in numerous articles and patents, and the application of these alloys for medical use is well advanced.

Andresson in U.S. Pat. No. 4,037,324 suggested the use of shape memory alloys for orthodontic arch wires, and since this early patent many other patents have issued claiming the advantages of using shape memory alloys for both orthodontic as well as medical components.

The driving force for making metal medical devices from shape memory alloys lies in their great resistance to permanent deformation as compared to conventional alloys employed in this application. Alloys used in conventional orthodontic arch wires and various medical instruments have relied on stainless steel, complex high nickel alloys such as Elgiloy™ and titanium based alloys, all of which can be given quite high yield strength through work hardening, but in use can be fairly easily permanently deformed. Normal metals, even with very high yield strength, cannot sustain strains much greater than 0.2% without suffering a permanent set. Once a bend or kink has been sustained in a medical instrument or device fabricated from one of the above conventional alloys it is virtually impossible to remove. The unusual property of pseudoelasticity exhibited by shape memory alloys such as Au—Cd, Cu—Zn—Al, Ni—Ti and many others makes possible the complete "elastic" recovery of strains as great as 10%. Due to its high recoverable strain and its excellent resistance to corrosion, the shape memory alloy of preference for orthodontic and medical components has been within the Ni—Ti family of alloys.

Shape memory alloys belong to a class which exhibit what is termed thermoelastic martensite transformation. The term martensite refers to the crystalline phase which is produced in steels when quenched from a high temperature. The phase which exists at the elevated temperature is referred to as austenite; these terms have been carried over to describe the transformations which occur in shape memory alloys. When a steel has been quenched from the austenitic temperature to martensite, to again form austenite requires heating the structure to quite high temperatures, usually in excess of 1400° F.

Figure 1:
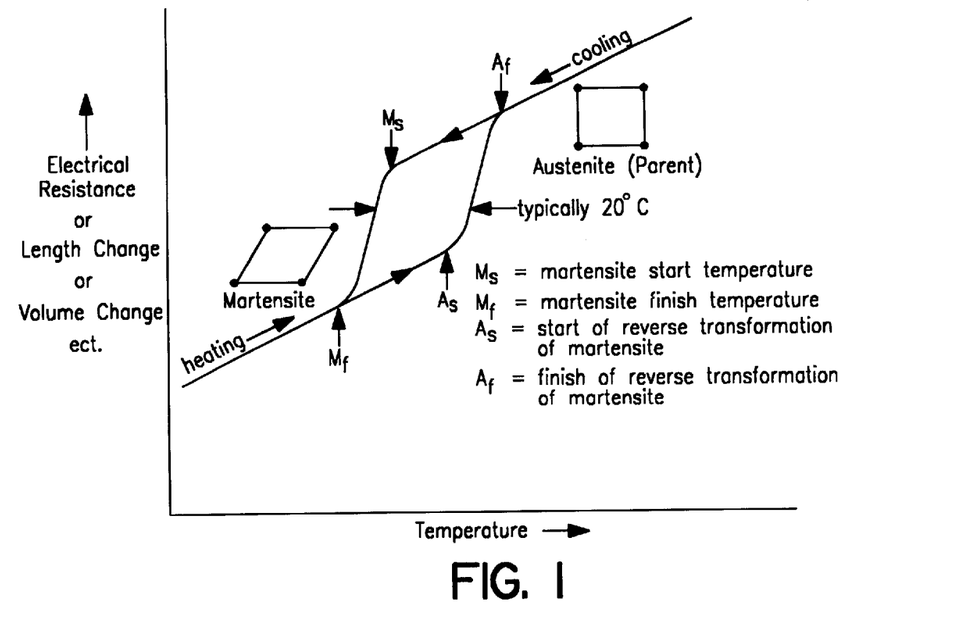
FIG. 1 is a hysteresis curve showing the transformation of a shape memory alloy.

By contrast, the thermoelastic shape memory alloys can change from martensite to austenite and back again on heating and cooling over a very small temperature range, typically from 18 to 55° F. The transformation of a shape memory alloy is usually described by its hysteresis curve, FIG. 1. In this figure it is shown that on cooling from the austenitic phase, often called the parent phase, martensite starts to form at a temperature designated as $M_S$ and upon reaching the lower temperature, $M_F$ the alloy is completely martensitic. Upon heating from below the $M_F$ temperature the martensite starts to revert to the austenitic structure at $A_S$ and when the temperature designated as $A_f$ is reached the alloy is completely austenitic. These two phases or crystalline structures have very different mechanical properties: the Young's Modulus of austenite is ~12×10$^6$ psi while that for martensite is ~4×10$^6$ psi. and the yield strength, which depends on the amount of cold work the alloy is given, ranges from 28 to 100 ksi for austenite and from 10 to 20 ksi for martensite.

Figure 2:
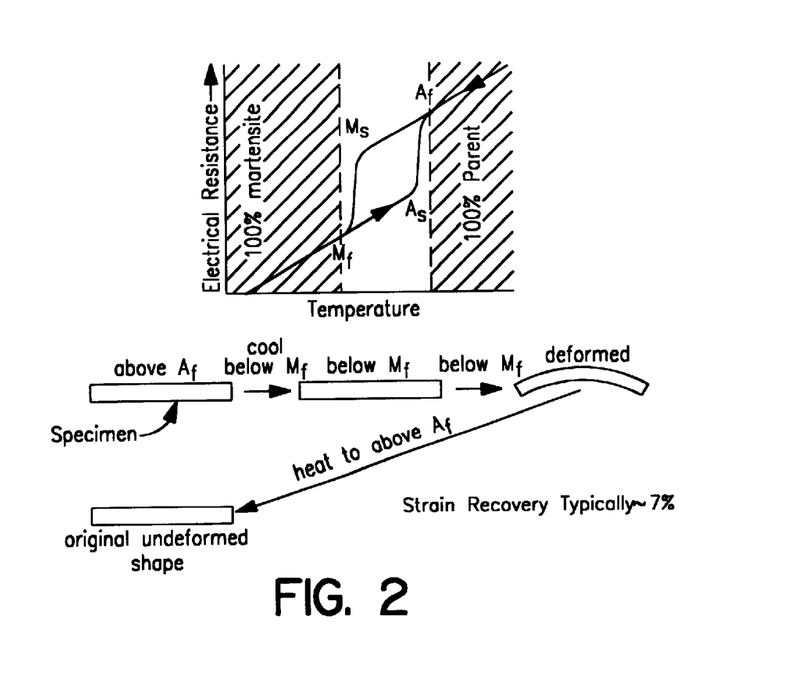
FIG. 2 is a schematic view of the process of the present invention.

The unique feature of shape memory alloys is their ability to recover deformation. When a shape memory alloy specimen, hereinafter referred to as SMA, in its martensitic form is subjected to stress, the strain is accommodated by the growth and shrinkage of individual martensite variants rather than by the mechanisms which prevail in conventional alloys: slip, grain boundary sliding and dislocation motion. When deformed martensite is heated to the austenite finish temperature $A_F$ the part reverts to its original undeformed state. This process is illustrated in FIG. 2.

Although this process could be utilized in medical devices to recover accidental bending and kinking, the mechanical properties of martensite, its yield strength and its modulus of elasticity, are too low for this application, and, in addition, heating medical devices is not a convenient process. Fortunately, another mode of deformation of SMAs provides the properties and behavior ideally suited to this service; this is pseudoelastic behavior.

Figure 3:
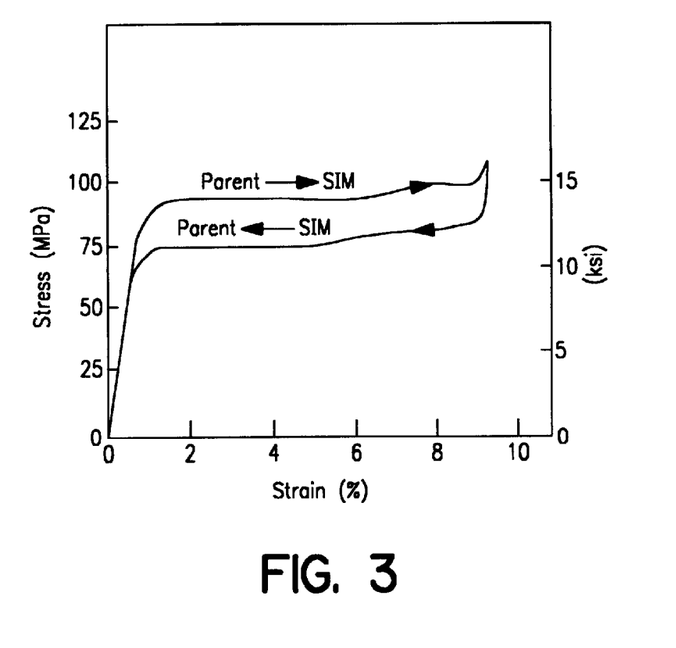
FIG. 3 is a curve showing the behaviour of SIM.
Figure 4:
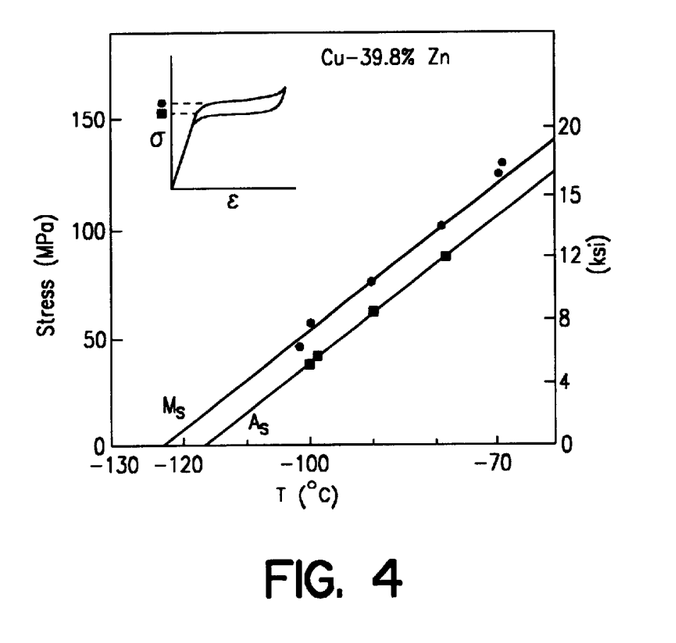
FIG. 4 is a curve showing the stress required to produce SIM and the temperature dependence of stress-induced martensite.
Figure 5:
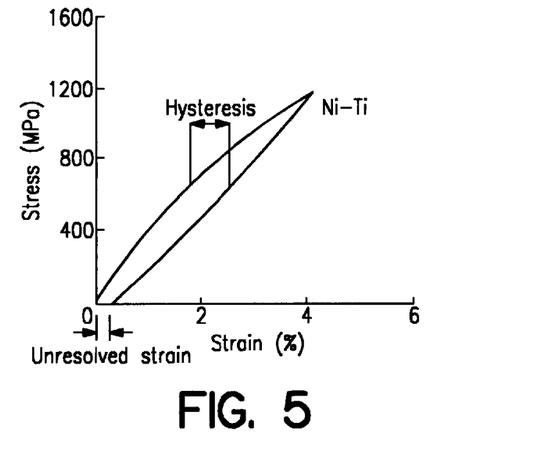
FIG. 5 is a stress-strain diagram for cold worked martensite yielding linear superelastic behaviour.
Figure 6:
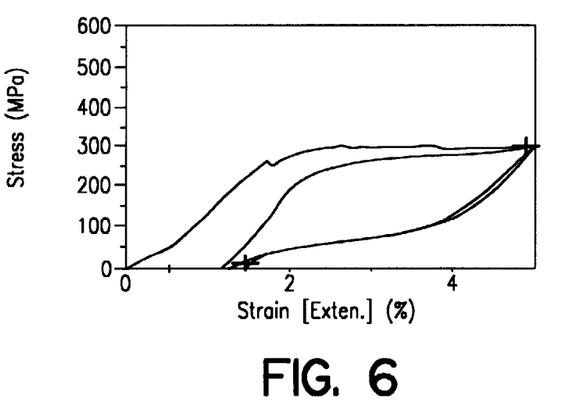
FIG. 6 is a stress-strain curve for the alloy with the treatment.
Figure 7:
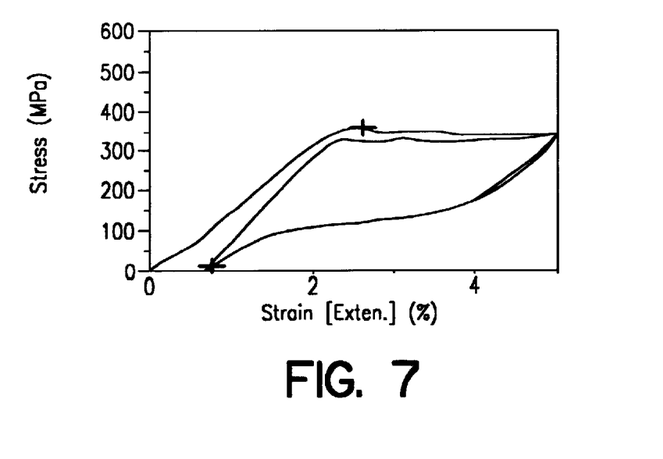
FIG. 7 is a stress-strain curve for the alloy of FIG. 6 tested at −10° C.
Figure 8:
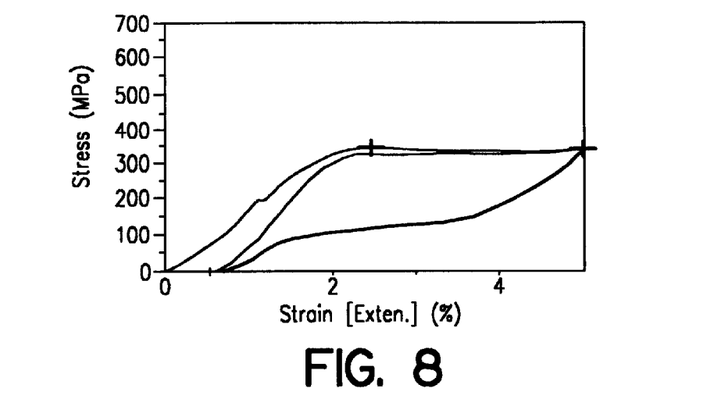
FIG. 8 is the stress-strain curve of the alloy of FIG. 6 tested at 0° C.
Figure 9:
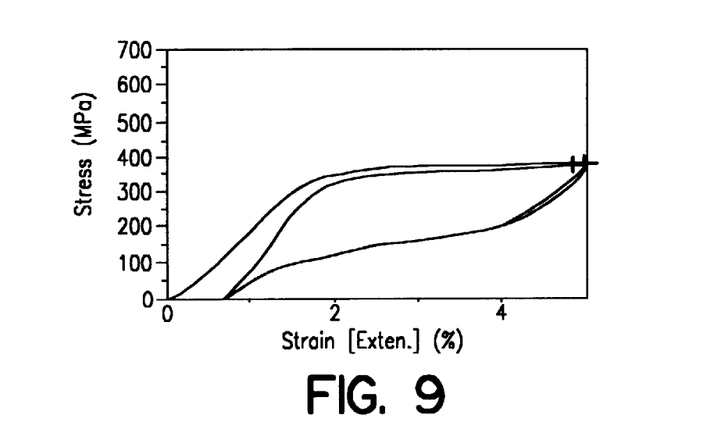
FIG. 9 is the stress-strain curve of the alloy of FIG. 6 tested at +10° C.
Figure 10:
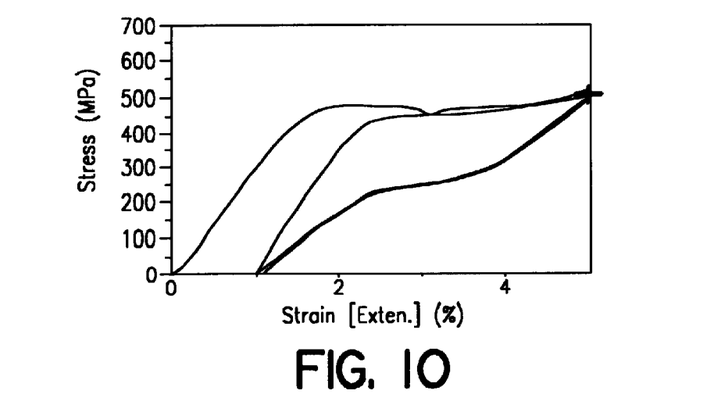
FIG. 10 is the stress-strain curve of the alloy of FIG. 6 tested at 30° C.
Figure 11:
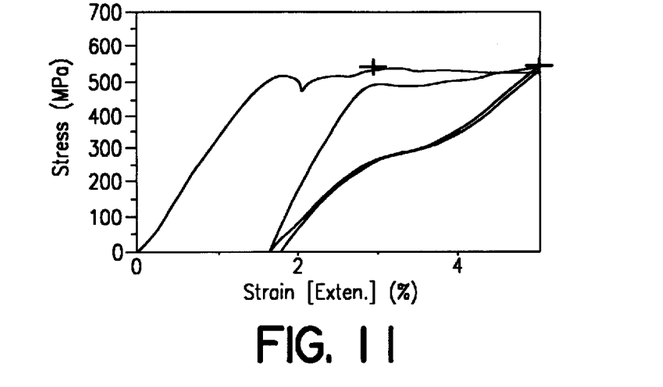
FIG. 11 is the stress-strain curve of the alloy of FIG. 6 tested at 40° C.
Figure 12:
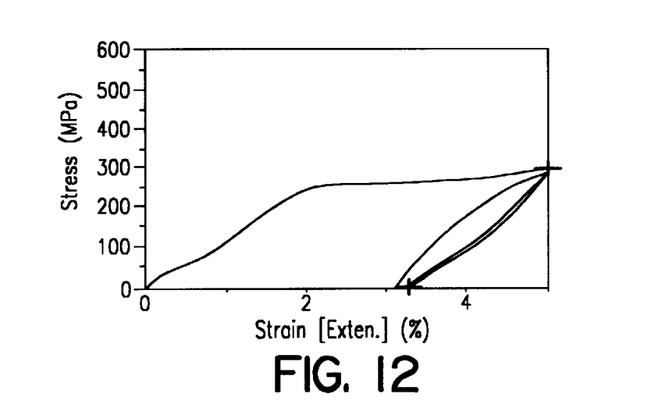
FIG. 12 is the stress-strain curve of the alloy with a different treatment from that of FIG. 6.
Figure 13:
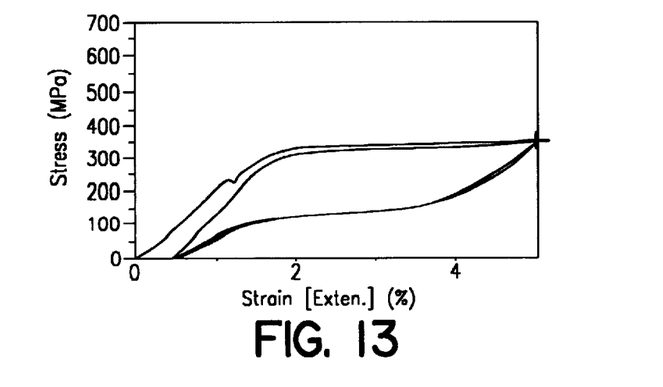
FIG. 13 is the stress-strain curve of the alloy of FIG. 12 tested at 0° C.
Figure 14:
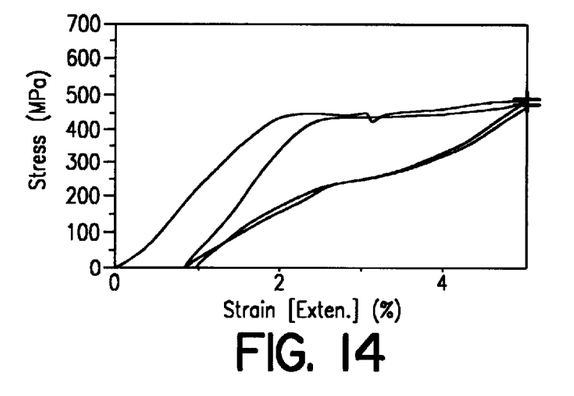
FIG. 14 is the stress-strain curve of the alloy of FIG. 12 tested at 25° C.
Figure 15:
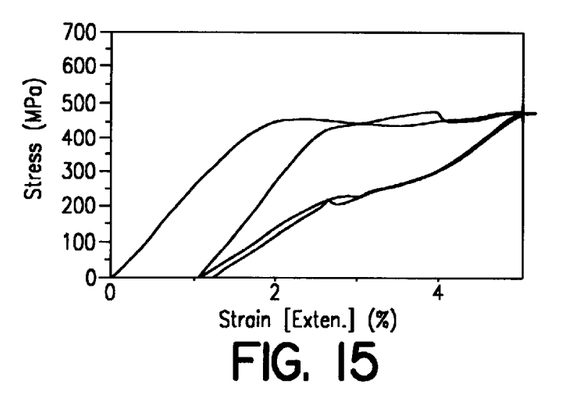
FIG. 15 is the stress-strain curve of the alloy of FIG. 12 tested at 30° C.
Figure 16:
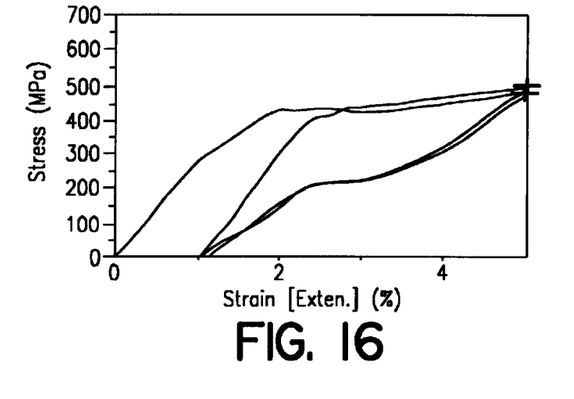
FIG. 16 is the stress-strain curve of the alloy of FIG. 12 tested at 40° C.

As indicated above, martensite forms when a SMA is cooled from the austenitic region to below the $M_S$ temperature; it can also form when the austenite is stressed to above some critical level. The martensite so formed is called stress-induced-martensite or SIM. Since the martensite formed under stress is at a temperature where it is not stable, when the stress is removed the alloy spontaneously reverts to its prior unstressed shape. This behavior is illustrated in FIG. 3. It can be observed that the reversion stress is lower than the stress at which martensite forms. These stresses are referred to as the upper and lower plateau stresses and their magnitude is dependent on the thermal and mechanical treatment which the SMA has received. As the temperature of the specimen is raised, the stress magnitude required to produce SIM is increased, as shown in FIG. 4, however when the specimen reaches a critical temperature above $A_F$, designated as $M_D$, stress induced martensite cannot be formed, no matter how high the stress. This behavior gives rise to a limitation on using the pseudoelastic property in many situations since it places a limit on the temperature range over which pseudoelasticity is observed; typically in the NiTi alloys, this is a temperature range of about 60° C. (108° F.), although a 40° C. (72° F.) range is more typical. The desirable temperature range for medical and orthodontic application is in the region of body temperature, +40° C.±10° C., readily achieved in these alloys.

Prior practitioners of the art of applying SMAs to medical and orthodontic components have resorted to the use of an SMA which has been cold worked in the martensitic state followed by a low temperature anneal to give a combination of shape memory behavior and superelastic characteristics. This processing gives a component with an elastic range of approximately 3% over a temperature range of −20 to +40° C. We have found that by using an alloy with higher than the equiatomic Ni/Ti ratio, subjecting it to a high temperature annealing followed by water quenching and a subsequent aging treatment, that we obtain a pseudoelastic behavior combined with excellent forming characteristics and a strain recovery of at least 3% over a temperature range from −20 to +40° C. The treated alloy yield strength ranges from 42 to 72 Ksi.

SUMMARY OF THE INVENTION

An object of the present invention is to provide a nickel-titanium alloy which is particularly useful for medical instruments and devices, as well as components thereof.

Another object of the present invention is to provide an alloy having pseudo-elastic properties and which is useful for medical instruments and devices, as well as components thereof.

A further object of the present invention is to provide a material for making medical instruments and devices as well as components thereof which are formable without the creation of cracks.

These and other objects of the present invention are accomplished by providing a nickel-titanium shape memory alloy which is especially useful in making medical instruments and devices, as well as components thereof and has desired pseudoelastic properties, characterized by:

allowing large plastic deformations during fabrication of the part before the desired pseudoelastic properties are established, having pseudoelastic properties without using cold working, having greater than 2.5% elasticity over the temperature range where these devices are usually located, and being capable of undergoing large amounts of cold or hot forming without danger of cracking/fracturing during the forming operations required to make the part.

The unusual property of pseudoelasticity exhibited by shape memory alloys such as Au—Cd, Cu—Zn—Al, Ni—Ti and many others makes possible the complete "elastic" recovery of strains as great as $10^5$. Due to its high recoverable strain and its excellent resistance to corrosion, the shape memory alloy of preference for medical instruments and devices, as well as components thereof has been within the Ni—Ti family of alloys.

The requirement of forming a medical instrument or devices, as well as components thereof from a piece of SMA wire or strip and controlling the amount of cold work it receives, both initially and in the final steps of component fabrication, followed by an annealing step which may require several hours, is considerably more complicated than the method of the present invention.

Prior practitioners of the art of applying SMAs to medical instruments and devices, as well as components thereof have recognised the temperature limitations discussed above and have resorted to the use of an SMA which has been cold worked in the martensitic state followed by a low temperature anneal to give a combination of shape memory behaviour and superelastic characteristics. This processing gives a component with an elastic range of approximately 3% over a temperature range of −20 to +40° C.

Nickel-titanium alloys rendered pseudoelastic by a combination of cold work and heat treatment have a high yield strength which must be reduced by an annealing treatment requiring long periods of time to arrive at a satisfactory yield strength for medical instrument and device service. If the starting material for forming the medical component has already been cold work then subsequent forging or forming of the part may result in breakage.

In pseudoelastic behaviour arising out of SIM, the upper plateau stress in this process can be changed by a combination of cold work following by an annealing treatment. Another form of superelastic behaviour is obtained when a shape memory alloy in the martensitic state is cold worked, yielding a material with the low modulus characteristic of martensite but with complete elastic behaviour up to a 4% strain. In addition, this behaviour is observed over a temperature range of from −200 to +150° C.

Past experiments on the precipitation hardening process, for instance by Nishida et al, Scripta Met, Vol 18, pp1299–1302, 1984, show that there is an optimum aging temperature to achieve the fine precipitates needed to increase austenite strengthening. Austenite yield strength must be high in order to have SIM proceed without having slip deformation of the matrix and permanent strain. A range of solution treatments and aging times and temperatures have been studied and reported in the literature for nickel titanium alloys.

The treatment and the alloy selection provided by the present invention is a modification of those commonly proposed. Prior studies have not provided detailed information on the temperature range over which the pseudoelastic behaviour is observed in alloys subjected to solution treatment and aging. With the treatment described, the present invention provides a method of producing a pseudoelastic nickel-titanium alloy which exhibits properties ideal for easy fabrication of medical instruments and devices as well as components thereof combined with those properties desired for a medical component which features high resistance to accidental damage.

The present invention provides using an alloy with higher than the equiatomic Ni/Ti ratio, subjecting it to a high temperature solution treatment at above 750° C., followed by water quenching, and a subsequent aging treatment, that a pseudoelastic behaviour is obtained combined with excellent forming characteristics and a strain recovery of at least 3% over a temperature range from −20 to +40° C. The treated alloy yield strength ranges from 42 to 72 Ksi.

One process to obtain pseudoelastic behaviour is by a solution heat treatment of a high nickel SMA at about 850° C. followed by water quenching and then precipitation hardening at a lower temperature. High nickel alloy means alloys with a nickel content in excess of 50.5 atomic %.

The present invention seeks to provide a shape memory alloy and process which reduces the complexity of producing components for medical devices by using a precipitation hardening treatment of a high nickel alloy rather than the presently used cold working and heat treating. The resulting components are characterised by pseudoelastic properties which dramatically reduce the chance for accidental deformation or kinking. The precipitation process combined with the particular nickel-titanium alloy composition employed features a relative low upper plateau stress which renders the components flexible which, in turn, make medical components fabricated in the described manner easy to use.

By contrast with the prior art, forming the medical components when the alloy of this invention has been solution treated is quite easy, since in this condition it has excellent ductility. After forming, the component is subjected to an aging treatment which gives the part the pseudoelastic properties desired in medical components.

Other objects, features and advantages will be apparent from the following detailed description of preferred embodiments taken in conjunction with the accompanying drawings in which:

DESCRIPTION OF THE INVENTION

The co-pending application of the present inventors filed May 14, 1999, entitled Eyeglasses and Parts Thereof Using Shape Memory Alloys is hereby incorporated herein by reference.

In the introduction to this specification the pseudoelastic behavior arising out of SIM is described. The upper plateau stress in this process can be changed by a combination of cold work followed by an annealing treatment. Another form of superelastic behavior is obtained when a shape memory alloy in the martensitic state is cold worked, yielding a material with the low modulus characteristic of martensite but with complete elastic behavior up to a 4% strain. In addition, this behavior is observed over a temperature range of from −200 to +150° C. An alternative process to obtain pseudoelastic behavior is by a solution heat treatment of a high nickel SMA at about 850° C. followed by water quenching and then precipitation hardening at a lower temperature. High nickel alloy means alloys with a nickel content in excess of 50.5 atomic %.

There is an optimum aging temperature to achieve the fine precipitates needed to increase austenite strengthening. Austenite yield strength must be high in order to have SIM proceed without having slip deformation of the matrix and permanent strain. The treatment and the alloy selection provided by the present invention differs from those commonly proposed. With this treatment the present invention provides a method of producing a pseudoelastic nickel-titanium alloy which exhibits properties ideal for easy fabrication of medical and orthodontic devices and components combined with those properties desired for these components which include good biocompatibility and corrosion resistance, high torqueability and high resistance to kinking.

The present invention seeks to provide a shape memory alloy and process which reduces the complexity of producing shape memory alloy components for medical and orthodontic devices and components by using a precipitation hardening treatment of a high nickel alloy rather than the presently used cold working and heat treating. The resulting components are characterized by pseudoelastic properties which dramatically reduce the chance for accidental deformation or kinking. The precipitation process combined with the particular nickel-titanium alloy composition employed features a relatively low upper plateau stress which renders the components flexible which, in turn, make the component very resistant to kinking.

Nickel-titanium alloys rendered pseudoelastic by a combination of cold work and heat treatment have a high yield strength which must be reduced by an annealing treatment requiring long periods of time to arrive at a satisfactory yield strength for medical and orthodontic service. If the starting material for forming the component has already been cold worked then subsequent forging or forming of the part may result in breakage.

By contrast, forming these components when the alloy of this invention has been solution treated is quite easy since in this condition it has excellent ductility. After forming, the component is subjected to an aging treatment which gives the part the pseudoelastic properties desired in orthodontic and medical components.

It is known that when the nickel content of a nickel-titanium alloy is higher than 50.5 At % then such an alloy can be strengthened by an age hardening process. In this method of treatment the alloy is first solution treated at a temperature in excess of 750° C. followed by water quenching. If the solution treated article is then heated to an intermediate temperature of from 300° C. to 600° C. a second phase of composition $TiNi_3$ is precipitated. By choosing the correct aging temperature and aging time, very fine precipitates are produced, giving rise to optimum properties.

Alloys with a composition in which nickel is present in excess of the stoichiometric ratio of 50/50 atomic percent, have low transformation temperatures, for example $A_s$ temperature lower than −20° C. Since in the present invention it is desired to have pseudoelastic properties to temperatures as low as −20° C., it is an additional advantage that the alloys capable of age hardening also have a low transformation temperature. The 50/50 atomic % alloy is by weight % 55Ni—45Ti. The alloy which has proven optimum for this application is one with a 56.1 wt % Ni and 43.9 wt % Ti. It should be understood that other high nickel NiTi binary compositions can also be used within the scope of the present invention, and that these alloys may have additions of Mo, Ta, Nb, Zr, Cu, Co, Fe, Cr, Mn or V as partial substitution for the nickel with similar results.

In one example of the present invention, NiTi alloy with a composition of 56.1 wt % Ni—43.9 wt % Ti is cold worked 29% and then solution treated at 850° C. for 30 minutes followed by water quenching. The specimen is then aged at 350° C. for 30 minutes and water quenched. The stress-strain curves for the alloy with this treatment are shown in FIGS. 6 through 11 for test temperatures from −20° C. to +40° C. After the first cycle there is a residual strain which ranges from 1.7% at 40° C. to 0.35% at 0° C. Subsequent cycles show a residual strain of approximately 0.15%. In all cases the recoverable strain is greater than 3%.

A NiTi alloy with the same composition as shown in FIGS. 6–11 is cold worked 29% and then solution treated at 850° C. for 30 minutes and water quenched. The specimen is then aged at a temperature of 350° C. for 60 minutes and water quenched. The stress-strain curves for alloy specimens with this treatment are shown in FIGS. 12 through 16 for test temperatures from −20° C. to +40° C. The longer aging times result in a greater residual strain after the first cycle but low residual strain in subsequent cycles; from 0.02 to 0.19. Although the recoverable strain in the 60 minute aging treatment is in excess of 4% in the temperature range from 0° C. to +40° C., at −20° C. the recoverable stain falls to 1.5%.

Figure 17:
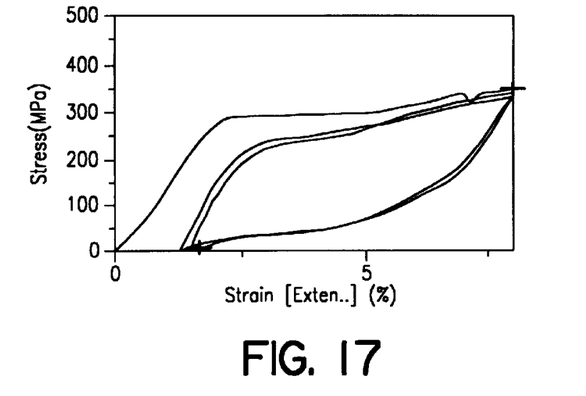
FIG. 17 is a stress-strain curve for the alloy with a modified treatment.
Figure 18:
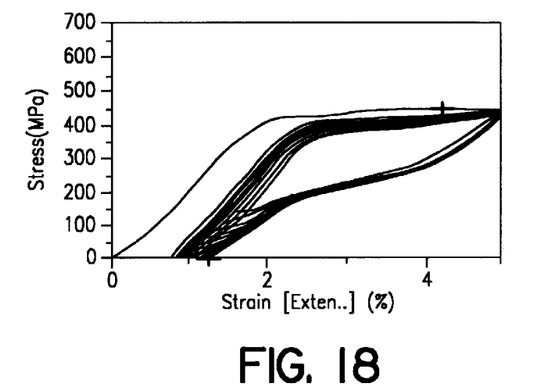
FIG. 18 is a stress-strain curve showing that performance is maintained over many cycles at 5% strain.
Figure 19:
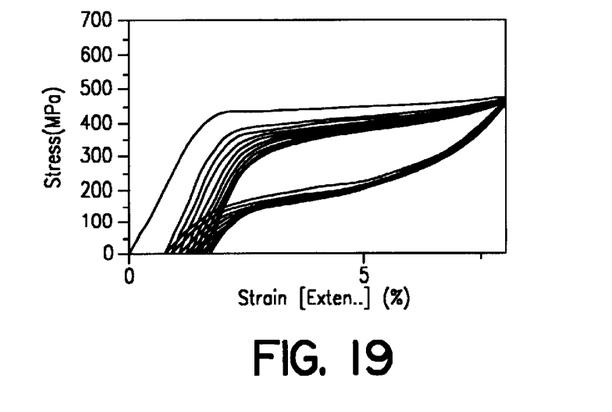
FIG. 19 is a stress-strain curve showing that performance is maintained over many cycles at 8% strain.

The use of the pseudoelastic NiTi in orthodontic and medical components assumes that in some cases the performance will be maintained after many cycles of deformation in use. To check this specimens were cycled 10 times at strains to 5% and at strains to 8%. The curves in FIGS. 17 and 18 show that the recoverable strain remains essentially constant, and the upper plateau stress also is essentially unchanged.

The testing of less Ni rich alloys, for example an alloy with 55.9 wt % Ni—44.1 wt % Ti did not result in pseudoelastic behavior as good as the alloy cited above. In addition, aging the first cited alloy at other temperatures, 300° C./30 min. or 60 min., 400° C./30 min or 60 min., and 450° C./30 min. or 60 min. did not give acceptable properties; as such, the 350° C. treatment vicinity is considered unique, and the alloy composition is considered optimum for this processing schedule.

A typical processing of some components requires different levels of cold work to achieve the desired end product. By using a solution treated high nickel alloy the effect of different levels of cold work generated during the forming operation is minimized. The final aging treatment renders the piece pseudoelastic and ready for any final processing steps such as plating, coating or joining.

It has been observed that a small amount of cold work before the aging treatment gives slightly better performance but this is not considered a necessary step in the normal processing of medical and orthodontic components of the type described below.

Orthodontic Appliances

The purpose of orthodontic appliances is to correct teeth irregularities and/or abnormalities in their relationships with surrounding members. This is achieved by using elastically deformed wires which impart forces to the targeted teeth and cause movements during the wire's unloading process.

Orthodontic materials have evolved over the years from simple stainless steels to high modulus cobalt alloys, low modulus titanium alloys of linear elasticity and duplex wires using either twisted, braided or coaxial configurations. Materials suitable for orthodontic appliance applications preferably possess a combination of high spring-back, low stiffness, reasonable formability, good corrosion resistance, and the ability to be readily joined to other components.

PE phenomenon has not been utilized in orthodontic arch wire application with the exception of NiTi alloy. NiTi, with its exceptionally high strain recovery of up to 8%, has long been used as orthodontic wire material, as was described in U.S. Pat. No. 4,037,324. But the material suffers from poor formability and difficulty in joining with other appliances. The availability of a low stiffness pseudo-elastic NiTi wire with better forming characteristics and the ability to be joined to other appliances would be of great value to the practicing orthodontist.

It has been recognized that optimal tooth motion is accomplished by the application of a low and constant force on the teeth, thus avoiding root resorption and hyalinization of the periodontal ligament which inhibit tooth motion. The control of the force delivered by the orthodontic appliance can be of two forms, variable cross section wire or variable modulus wires. The latter approach, referred to as variable-modulus technique [C.J. Burstone, American J. Orthodontics, vol. 80, 1981, p1.], has proven more popular with the availability of wires having a wide variety of elasticity and stiffness. Instead of using one type of wire material and varying the desired mechanics by changing the wire dimension, variable-modulus technique has the freedom in selecting wire material which yields the optimum force/deflection characteristics for each stage of the orthodontic practice while maintaining the same wire dimension. This technique significantly reduces appliance complexity and creates greater flexibility in clinical practices.

Stents

Stents are fabricated from coiled wire springs or from laser cut tube and are used to repair the patency of previously weakened, narrowed, ballooned or other wise defective or impaired lumen or other body channels. They are deployed by the use of a catheter in laproscopic procedures. Examples are: blood vessels, bile duct, esophagus, urethra, trachea and the like. Specifically: interluminal lining of Aortic Abdominal aneurysms, iliac or femoral aneurysms, recanalization of injured vessels caused by blunt or penetrating trauma, dilation and recanalization of stenotic arterial segments, tampanade and obliteration of esophageal varices, recanalization of esophageal stenoses secondary to carcinoma or benign strictures, ureteral strictures and tracheal strictures. In all these applications a super-elastic shape memory alloy with improved fabricability would be advantageous as compared to current manufacturing practice.

Catheter Introducers

Interventional cardiovascular procedures require the use of catheters to bring to the area of interest either instruments for measuring and observing the affected area or to deploy stents. The tortuous paths of many of the body vessels require the use of a guiding system to make possible the continuous advance of the catheter; these guide wires are called catheter introducers and two characteristics are required: flexibility and freedom from any tendency to kink and the ability to faithfully transmit a twisting motion from the distal to the proximal end. Super-elastic shape memory alloy wires have demonstrated these characteristics and are the preferred material for construction Oral, Maxillofacial Reconstructive Procedures Using Pins and Plates Many cosmetic procedures such as reshaping mandible, frontal bones, nose, and cranial features frequently require auxiliary fixtures to support the new position during bone setting. Since in some cases these plates and fixtures have complex shapes, the ease of fabrication offered by the disclosed processing is an advantage Oviduct Clamp The clamping of a fallopian tube using endoscopic procedures is well established and the use of shape memory clamps is a preferred technique. The ease of fabrication offered by the disclosed process makes possible the ready fabrication of this type of device.

Bone Staples

Shape memory staples have been proposed for bringing into close proximity fractured surfaces of various bones. Fabrication of these devices using the disclosed process offers the advantage of batch manufacturing.

The advantages referred to the above noted uses are examples and many other similar surgical devices can benefit from a readily fabricated shape memory or PE alloy. Examples of environments in which the alloy of the present invention could be used are disclosed in the following U.S. Pat. No. 4,503,569 for a graft prosthesis, U.S. Pat. No. 5,147,370 for a stent, U.S. Pat. No. 5,466,242 for a stent for biliary, urinary or vascular system, U.S. Pat. No. 5,653,689 for an infusion catheter, and U.S. Pat. No. 5,830,179 for a urological stent.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

We claim:

1. In a medical or orthodontic component or device having at least a portion thereof fabricated from Ni—Ti based shape memory alloy, the improvement comprising:
   (a) said alloy being more than 50 atomic % nickel;
   (b) said alloy having been solution treated at a temperature of 650 to 1100° C. for 10–60 minutes;
   (c) after cooling, said alloy having been aged by heating it at a temperature of approximately 350° C. for 10–60 minutes;
   (d) said portion being characterized by:
      (i) having pseudoelastic properties without cold working,
      (ii) having greater than 2.5% elasticity over a temperature range of –20° C. to +40° C., and
      (iii) allowing large plastic deformations during the fabrication of said portion.

2. A component or device as defined in claim 1, characterized by being capable of large amounts of cold forming without danger of cracking or fracture during forming operations in its solution treated condition which are required to make orthodontic and medical components.

3. A component or device as defined in claim 2 wherein said portion is an orthodontic component.

4. A component or device as defined in claim 2 wherein said portion is a stent.

5. A component or device as defined in claim 2 wherein said portion is at least one selected from the group consisting of: a catheter introducer; oral maxillofacial reconstructive procedures using pins and/or plates; an oviduct clamp; a bone staple; a graft prosthesis; a stent for biliary, urinary or vascular system; an infusion catheter; and a urological stent.

6. A component or device as defined in claim 2, wherein said alloy composition is about 56.1 wt % NI—43.9 % Ti, which is solution treated at a temperature of 850° C. and subsequently water quenched and which can be readily cold formed in this condition, and which is subsequently aged at 350° C. generates pseudoelastic behavior in the component which is observed over the temperature range of –20° to +40° C.

7. A component or device as defined in claim 6, wherein said portion has been solution treated for about 30 minutes, and has been aged for about 30 minutes.

8. A component or device as defined in claim 7 wherein said portion has been cold worked about 20% before the solution treatment whereby the temperature range of the pseudoelastic performance is extended.

9. A component or device as defined in claim 7, wherein the relatively small amounts of cold work before the ageing treatment do not exceed 30%.

10. A component or device as defined in claim 2 wherein said portion is further characterized by a pseudoelastic or superelastic behaviour over the temperature range from –20° C. to +40° C.

11. A component or device as defined in claim 10 wherein the shape memory portion exhibits pseudoelastic properties with an upper plateau stress which is between approximately 42 Ksi and 72 Ksi, whereby the stress level is well suited for orthodontic and medical components.

12. A component or device as defined in claim 10 wherein there has been cold work of about 10–15% either before or after aging treatment and this has little effect on the pseudoelastic properties except for a slight improvement in this property.

13. A component or device as defined in claim 10 wherein the aging treatment has provided stress relief after secondary operations such as coating, plating or joining while at the same time imparting the desired pseudoelastic properties.

14. A component or device as defined in claim 10 characterized by the portion having been subjected to various cold work levels during fabrication to create various cross section of the design and after aging treatment exhibiting substantially uniform pseudoelastic properties.

15. A component or device as defined in claim 10 which exhibits pseudoelasticity at ambient and/or body temperature.

16. A component or device as defined in claim 10 wherein said portion is one selected from the group consisting of orthodontic arch wire, springs, implants, endodontic files.

17. A component or device as defined in claim 10 wherein said portion is characterized by having super-elastic properties by having been solution treated and aged, and exhibiting complete elastic behavior at strains up to 4%, thereby permitting the designing of medical instruments and devices which are resistant to permanent deformation or kinking.

18. A component or device as defined in claim 1, wherein said alloy portion has additional alloying elements, which, without substantially altering the processing of the portion, extend the temperature range of the pseudoelastic behaviour of the portion, and wherein said additional alloying elements are at least one selected from the group consisting of Ta, Mo, Nb, Co, Cr, Cu, V, Mn and Fe.

19. A method of making at least a component of a medical or orthodontal instrument or device, comprising:
 (a) fabricating said component of an alloy which includes
  (i) an alloy of NiTi with a higher nickel content than an equiatomic Ni/Ti ratio in a Ni—Ti shape memory alloy,
  (ii) and which has been solution treated at a temperature of 650 to 1100° C. for 10–60 minutes; and
 (b) aging said component after it is fabricated, by heating it at a temperature of approximately 350° C. for 10–60 minutes,
 said portion being characterized by:
  having pseudoelastic properties without could working, having greater than 2.5% elasticity over a temperature range of −20° C. to +40° C., and
  allowing large plastic deformations during the fabrication step before the desired pseudoelastic properties are established.

20. A method as defined in claim 19, wherein said step of fabricating includes large plastic deformations of said alloy before pseudoelasticity is imparted to the component.

21. A method as defined in claim 20, wherein said NiTi based shape memory component is characterised by having pseudoelastic properties without using cold working and greater than 2.5% elasticity over the temperature range of −20to +40° C.

22. A method as defined in claim 19, wherein said component is formed into an orthodontic arch wire.

23. A method as defined in claim 19, wherein said component is formed into an a medical device for use within a living body.

24. A method as defined in claim 19, wherein said component is formed into a medical device chosed from the group consisting of: (1) a stent; (2) a catheter introducer; (3) oral poins and/or plates used in maxillofacial reconstructive procedures; (4) an oviduct clamp; and (5) bone staples.

* * * * *